(12) United States Patent
Ohnuma et al.

(10) Patent No.: US 6,540,357 B1
(45) Date of Patent: Apr. 1, 2003

(54) GLAUCOMA DIAGNOSIS APPARATUS

(75) Inventors: Kazuhiko Ohnuma, Sodegaura (JP);
Yasufumi Fukuma, Tokyo (JP);
Hidetaka Aeba, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 9 days.

(21) Appl. No.: 09/715,125

(22) Filed: Nov. 20, 2000

(30) Foreign Application Priority Data

Nov. 18, 1999 (JP) ............................................. 11-327805

(51) Int. Cl.[7] ................................................ A61B 3/10
(52) U.S. Cl. ...................................... 351/215; 351/221
(58) Field of Search ................................ 351/200, 205, 351/206, 213, 215, 216, 221, 246

(56) References Cited

U.S. PATENT DOCUMENTS

| | | | | |
|---|---|---|---|---|
| 5,177,511 A | * | 1/1993 | Feuerstein et al. | 351/205 |
| 5,303,709 A | * | 4/1994 | Dreher et al. | 351/206 |
| 5,787,890 A | * | 8/1998 | Reiter et al. | 351/215 |
| 5,822,035 A | * | 10/1998 | Bille | 351/215 |
| 5,880,813 A | * | 3/1999 | Thall | 351/206 |
| 6,027,216 A | * | 2/2000 | Guyton et al. | 351/200 |
| 6,112,114 A | * | 8/2000 | Dreher | 351/215 |

* cited by examiner

Primary Examiner—Marvin M. Lateef
Assistant Examiner—John R. Sanders
(74) Attorney, Agent, or Firm—Oblon, Spivak, McClelland, Maier & Neustadt, P.C.

(57) ABSTRACT

A glaucoma diagnosis apparatus for determining thickness of nerve fiber layers. The apparatus includes an illuminating optical system for illuminating the ocular fundus of an eye to be examined with circularly polarized illuminating light and an imaging optical system including a CCD camera for photographing the image of an ocular fundus based on the reflected illuminating light from the ocular fundus and has a polarizing filter provided integrally with the imaging surface of the CCD camera. The filter includes repetitions of a unit platelet having a couple of polarizing microplates which transmit those linearly polarized light components crossing with each other out of the reflected illuminating light and adjacent polarizing microplates which transmit linearly polarized light components in direction crossing with both of the above/mentioned linearly polarized light components of the reflected illuminating light. Evaluation of a phase change of the circularly polarized illuminating light can be used to determine the nerve fiber layer thickness.

7 Claims, 8 Drawing Sheets

GLAUCOMA DIAGNOSIS APPARATUS

BACKGROUND OF THE INVENTION

1. Field of the Invention

The present invention relates to a glaucoma diagnosis apparatus suited for use in diagnosing glaucoma.

2. Prior Art

In the field of medical ophthalmology, glaucoma is known as a disease resulting from excavation or deficiency in the nerve fiber layers as caused by increased intraocular pressure, among others. At an advanced stage, glaucoma causes irreversible vision disorder, leading to loss of sight. Therefore, early discovery of signs of glaucoma is regarded as an urgent task. However, the nerve fiber layers vary in thickness from portion to portion on the ocular fundus and the progress of the defect of the nerve fiber layers is generally gradual until the morbid condition becomes severe, so that even when the fundus image is available as a result of ophthalmography of the fundus of a patient at an early symptom stage, it is difficult for an oculist to judge, based on that image, whether there is a defective area in the nerve fiber layers.

Meanwhile, it is known that the nerve fiber layers are a birefringent substance showing different refractive indices according to the direction of vibration (polarization) of light.

Thus, when the nerve fiber layers are irradiated with a polarized laser beam, the polarized light components pass through that layer at different velocities, resulting in different times for passing through the nerve fiber layer for each of the components of the polarized laser beam (phase difference).

The magnitude of this phase difference is positively correlated with the thickness of the nerve fiber layers at the portion through which the light has passed.

The polarized light is classified simply into linearly polarized light, circularly polarized light and elliptically polarized light according to the quantity of phase difference between the polarized light components.

Utilizing this fact, a glaucoma diagnosis apparatus has been developed which converts a laser beam from a laser diode to the linearly polarized state by means of a polarizing filter having linearly polarizing characteristics, modulates this laser beam to circularly polarized light using a quarter wavelength plate, deflects that laser beam by means of a scanning unit to scan the ocular fundus therewith, detects the rate of change in phase difference of the light reflected from the ocular fundus and determines the thickness of the nerve fiber layers.

However, this glaucoma diagnosis apparatus in the prior art can only scan a certain narrow area of the ocular fundus and cannot examine a wide area at a time. It has another problem that the data cannot be obtained as image information.

A further problem is that such a glaucoma diagnosis apparatus tends to be expensive and is still hardly available for ordinary ophthalmologists.

Accordingly, it is an object of the present invention, which has been made in view of the limitations of the related art discussed above, to provide a glaucoma diagnosis apparatus capable of determining the thickness of the nerve fiber layers in a simple, easy, and inexpensive manner by improving the optical system of a currently existing retinal or fundus camera in common use.

SUMMARY OF THE INVENTION

The glaucoma diagnosis apparatus according to one aspect of the invention comprises an illuminating optical system for illuminating the ocular fundus of a subject to be examined with circularly polarized illuminating light and an imaging optical system including a CCD camera for photographing the image of an ocular fundus based on the reflected illuminating light from said fundus, characterized in that said CCD camera has a polarizing filter provided integrally with the imaging surface of said CCD camera and said filter is composed of repetitions of a unit platelet being a couple of polarizing microplates one of which transmits one of said linearly polarized light components crossing with each other of said reflected illuminating light and another adjacent polarizing microplate which transmits linearly polarized light components whose direction is crossing to both of said linearly polarized light components of the reflected illuminating light. It is desirable that this glaucoma diagnosis apparatus comprises an illuminating optical system for illuminating the ocular fundus of a subject to be examined with circularly polarized illuminating light and an imaging optical system including a CCD camera for photographing the image of an ocular fundus based on the reflected illuminating light from said fundus, characterized in that said CCD camera has a polarizing filter provided integrally with the imaging surface of said CCD camera and said filter is composed of repetitions of a unit platelet being a couple of polarizing microplates one of which resolves one of said linearly polarized light components crossing with each other of said reflected illuminating light and another adjacent polarizing microplate which resolves said reflected illuminating light into linearly polarized light components crossing orthogonally with each other and adjacent polarizing microplates resolving the above reflected illuminating light into linearly polarized light components crossing with both of said linearly polarized light components mentioned above.

The glaucoma diagnosis apparatus defined in the above aspect of the invention is further provided in that said linearly polarized light component which is crossing to both of said linearly polarized light components is in the direction of 45° relative to both of said linearly polarized light components, and each polarizing microplate corresponds to each pixel of said CCD camera.

The glaucoma diagnosis apparatus according to another aspect of present invention comprises an illuminating optical system for illuminating the ocular fundus of a subject to be examined with circularly polarized illuminating light and an imaging optical system including a CCD camera for photographing the image of an ocular fundus based on the reflected illuminating light from said fundus, characterized in that the imaging optical system is provided at a position conjugated with the imaging surface of said CCD camera with a polarizing filter composed of repetitions of a unit platelet being a couple of polarizing microplates one of which resolves said reflected illuminating light into linearly polarized light components crossing diagonally with each other and another polarizing microplate which resolves said reflected illuminating light into linearly polarized light component having a direction crossing with both of said linearly polarized light components.

The glaucoma diagnosis apparatus defined in the above aspect is further provided in that the linearly polarized light component in the direction crossing with both of the above-mentioned linearly polarized light components is in the direction of 45° relative to both of the above linearly polarized light components and that each polarizing microplate corresponds to a pixel of the CCD camera.

The glaucoma diagnosis apparatus defined in the above aspect is more further provided in that a shape of elliptically polarized light is computed based on magnitude of the output of each pixel corresponding to each polarizing microplate constituting said unit platelet and thickness of the nerve fiber layers of said ocular fundus is determined based on said shape of the elliptically polarized light.

The glaucoma diagnosis apparatus defined in the above aspect is further provided in that said polarizing filter is arranged insertably into and retractably from the optical path of said imaging optical system.

The glaucoma diagnosis apparatus according to other aspect of the present invention comprises an illuminating optical system for illuminating the ocular fundus of a subject to be examined with circularly polarized illuminating light and an imaging optical system for photographing the image of an ocular fundus based on the reflected illuminating light from said fundus, characterized in that said imaging optical system is provided with a resolving optical system which resolves said reflected illuminating light into linearly polarized light components crossing diagonally with each other and another resolving optical system which resolves said reflected illuminating light into linearly polarized light component having a direction crossing with both of said linearly polarized light components, and each resolving optical system is provided with a CCD camera for photographing the fundus image based on the reflected illuminating light resolved into the respective linearly polarized light components.

The glaucoma diagnosis apparatus defined in the above aspect of the invention is further provided in that the direction of said linearly polarized light component which is crossing to both of said linearly polarized light components is in the direction of 45° relative to both of said linearly polarized light components.

The glaucoma diagnosis apparatus in accordance with further aspect of the invention comprises an illuminating optical system for illuminating the ocular fundus of a subject to be examined with circularly polarized illuminating light and an imaging optical system including a CCD camera for photographing the image of an ocular fundus based on the reflected illuminating light from said fundus, characterized in that the imaging optical system is provided with a rotatable polarizing filter which transmits linearly polarized light components of said reflected illuminating light.

The glaucoma diagnosis apparatus defined in the above aspect of the invention is further provided in that a green filter for transmitting green light is provided in the above-mentioned illuminating optical system.

By using the glaucoma diagnosis apparatus defined in one of the above aspects of the invention, it is possible to measure the thickness of the nerve fiber layers by improving the optical system of an existing fundus camera.

BRIEF DESCRIPTION OF THE DRAWINGS

FIG. 7 is an explanatory drawing illustrating the state of polarization of the reflected illuminating light from the ocular fundus of a subject to be examined, wherein (a) shows the circularly polarized illuminating light, (b) the state of polarization of the illuminating light reflected from the ocular fundus portion Hkl' and (c) the state of polarization of the illuminating light reflected from the ocular fundus portion Hkl".

In the figures, the reference numeral 5 denotes a CCD camera, 5a an imaging surface, 20 an illuminating optical system, 21 an imaging optical system and 42 a polarizing filter, and the symbol FB denotes a fundus image.

DESCRIPTION OF PREFERRED MODES OF EMBODIMENT

[Embodiment 1 of the invention]

Figure 1:
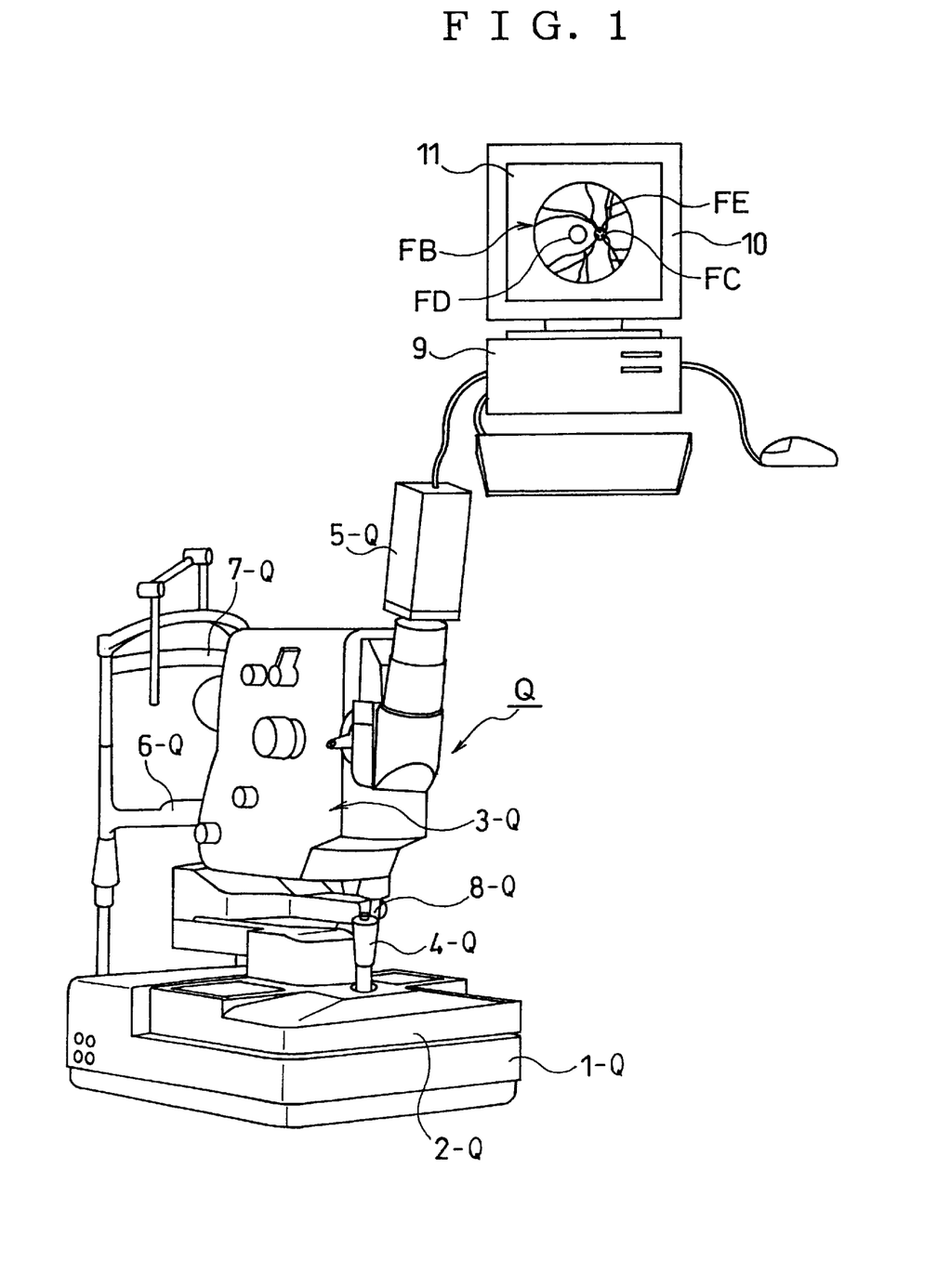
FIG. 1 is an external view of a typical fundus camera used in ocular fundus photography.

FIG. 1 shows an example of the fundus camera Q to be used in the glaucoma diagnosis apparatus of the invention. In FIG. 1, 1-Q denotes a base, 2-Q a stand, 3-Q the main body, 4-Q a joystick. 5-Q a CCD camera, 6-Q a jaw support, and 7-Q a forehead stopper, and these constituents are already known.

With this fundus camera Q, a patient puts their jaw on the jaw support 6-Q and their forehead on the forehead stopper 7-Q and looks at a fixed point in a predetermined direction by means of an internal fixation point lamp for fixation of patient's eye sight. Upon turning an imaging switch 8-Q to "on", the ocular fundus of a subject to be examined is illuminated by an illuminating optical system to be mentioned later herein and a fundus image is recorded by the CCD camera 5-Q of an imaging optical system to be mentioned later herein.

This CCD camera 5-Q is connected, for example, with a personal computer 9 constituting a part of the glaucoma diagnosis apparatus and the fundus image is stored in a frame memory of the personal computer 9. In place of storing the fundus image in a frame memory of the personal computer 9, the image may be recorded and stored in a hard disk, magnetic disk, floppy disk or optical magnetic disk.

An image display monitor 10 is connected with the personal computer 9 and, upon operation by means of a mouse, keyboard or the like, the stored fundus image FB is displayed on a screen 11. On the screen, FC denotes a mammilla, FD a macula of retina and FE a vascular vessel.

Figure 2:
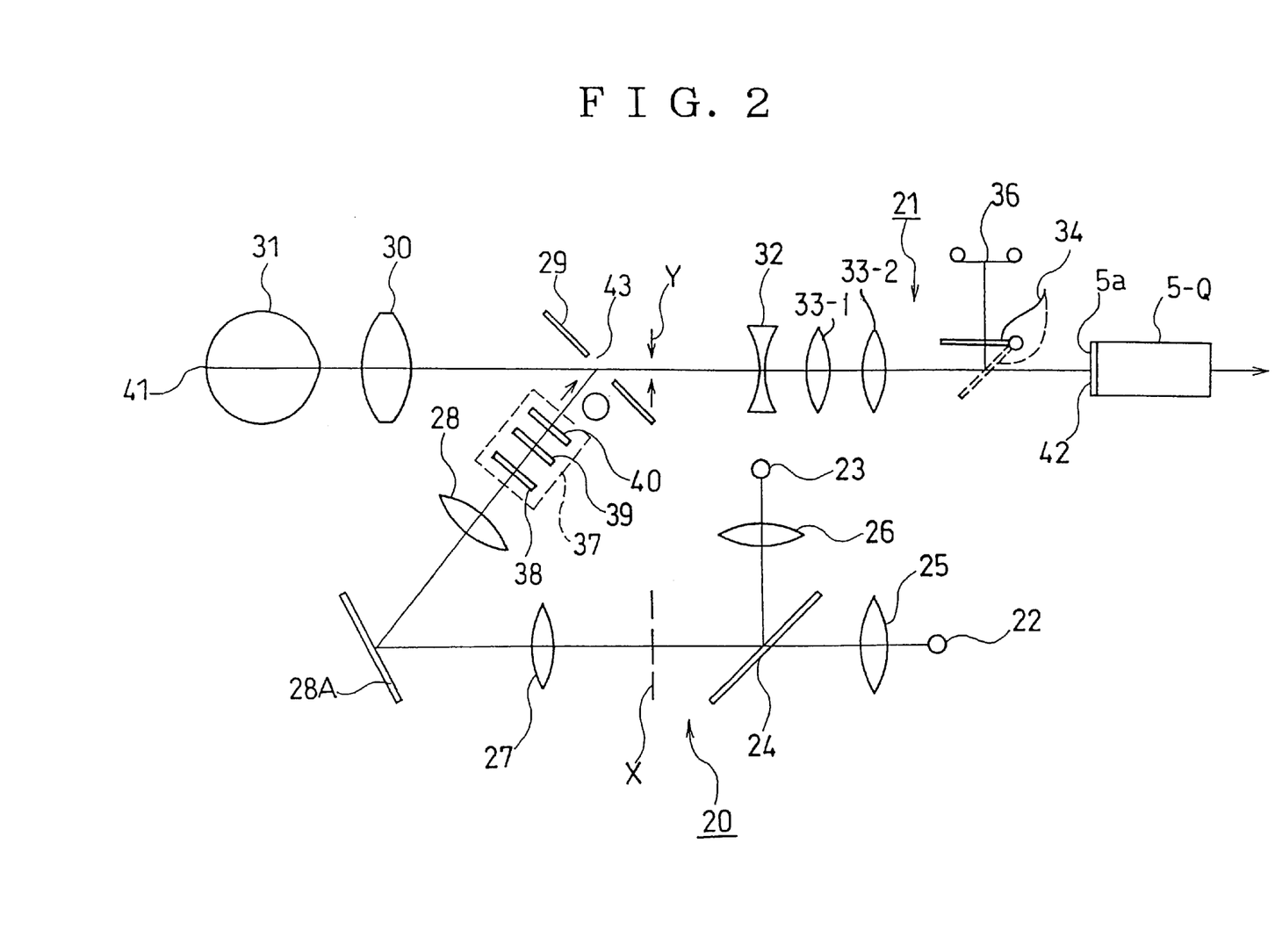
FIG. 2 is a schematic illustration of the optical system of the fundus camera shown in FIG. 1.

FIG. 2 shows the optical system of the fundus camera Q. In FIG. 2, 20 denotes an illuminating optical system and 21 an imaging optical system. The illuminating optical system 20 comprises a xenon lamp 22 and a halogen lamp 23 and the xenon lamp 22 and halogen lamp 23 are disposed in conjugated positions relative to a half mirror 24, and the xenon lamp 22 and halogen lamp 23 are relayed by means of condenser lenses 25 and 26 to the vicinity of a ring diaphragm X. This ring diaphragm X is relayed, through a relay lens 27, a total reflection mirror 28A, a relay lens 28, a perforated mirror 29 and an objective lens 30, to the vicinity of the pupil of an eye 31 to be examined in the same manner as with an ordinary fundus camera.

The imaging optical system 21 comprises an objective lens 30 facing the eye 31 to be examined, the perforated mirror 29, a focusing lens 32, relay lenses 33 (e.g., lens 33-1 and lens 33-2), a quick return mirror 34, a CCD camera 5-Q and a photographic film 36. The symbol 5a denotes the imaging surface of the CCD camera 5-Q. The photographic film 36 and the imaging surface 5a are conjugated with respect to the quick return mirror 34. On the occasion of taking a photograph on the film, the quick return mirror 34 is inserted into the optical path between the relay lenses 33 and CCD camera 5-Q, as indicated by a broken line and, on the occasion of observation or photographing by the CCD camera 5-Q, the mirror 34 is removed from the optical path.

Between the relay lens 28 and perforated mirror 29, there is detachably disposed a polarizing unit 37 in the optical path of the illuminating optical system 20. This polarizing unit 37 is composed of a green filter 38, a polarizing filter 39 having linearly polarizing characteristics and a quarter-wave plate 40. During observation of the ocular fundus 41 of the eye 31 to be examined, the polarizing unit 37 is kept removed from the optical path of the illuminating optical system 20.

Figure 3:
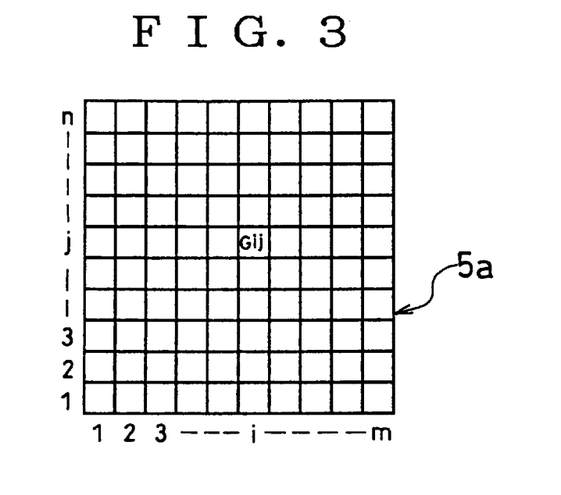
FIG. 3 is an explanatory drawing of the imaging surface of the CCD camera shown in FIG. 2.
Figure 4:
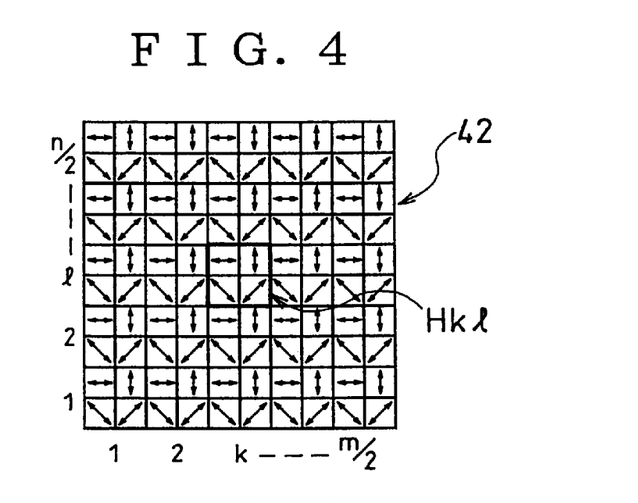
FIG. 4 is an explanatory drawing of the polarizing filter shown in FIG. 2.

The imaging surface 5a of the CCD camera 5-Q is composed of a number of pixels Gij (i=1,2, ..., m;j=1, 2, ..., n), as shown in FIG. 3. In front of the imaging surface 5a, there is integrally provided a polarizing filter 42. This polarizing filter 42 is constituted by arranging unit platelets Hkl (k=1, 2, ..., m/2; l=1, 2, ..., n/2) in the vertical and horizontal directions, as shown in FIG. 4. Each unit platelet Hkl is composed of polarizing microplates Hkl1 and Hkl2 adjacent to each other and dividing the reflected illuminating light into linearly polarized light components orthogonal to each other (transmitting linearly polarized light components crossing with each other out of the reflected illuminating light) and polarizing microplates Hkl3 and Hkl4 dividing the reflected illuminating light into linearly polarized light components crossing with both of the linearly polarized light components mentioned above (transmitting linearly polarized light components in the directions crossing with both of the linearly polarized light components mentioned above), as enlargedly shown in FIG. 5. In this case, the directions of the linearly polarized light components transmitted by the polarizing microplates Hkl3 and Hkl4 are at an angle of 45° with respect to the linearly polarized light components transmitted by the polarizing microplates Hkl1 and Hkl2. The polarizing microplates Hkl1 and Hkl4 correspond to the pixels Gij, respectively.

For observing the ocular fundus, the halogen lamp 23 is switched on, the polarizing unit 37 is removed from the optical path of the illuminating optical system 20, and the ocular fundus41 is illuminated with ring-shaped illuminating light. The reflected illuminating light from the ocular fundus 41 is led, through the objective lens 30, the opening 43 of the perforated mirror 29 and an imaging diaphragm Y, to the focusing lens 32, and further to the imaging surface 5a through the relay lenses 33 and polarizing filter 42 and forms an image on the surface 5a, and the fundus image FB is displayed on the screen 11.

In ophthalmography for glaucoma diagnosis, the polarizing unit 37 is inserted into the optical path of the illuminating optical system 20. When the xenon lamp 22 is caused to emit light, the illuminating light therefrom is led, through the condenser lens 25, half mirror 24, ring-form diaphragm X, relay lens 27, total reflection mirror 28A and relay lens 28, to the polarizing unit 37. The green filter 38 transmits green wavelength light, while it cuts light in other wavelength ranges. The green wavelength light is linearly polarized by the polarizing filter 39. The linearly polarized green wavelength light is converted to circularly polarized light by a quarter-wave plate 40. This circularly polarized green wavelength light is reflected by the perforated mirror 29 and passes through the objective lens 30 to become ring-shaped illuminating light and illuminate the ocular fundus 41 through the pupil of the eye 31 to be examined.

Figure 6:
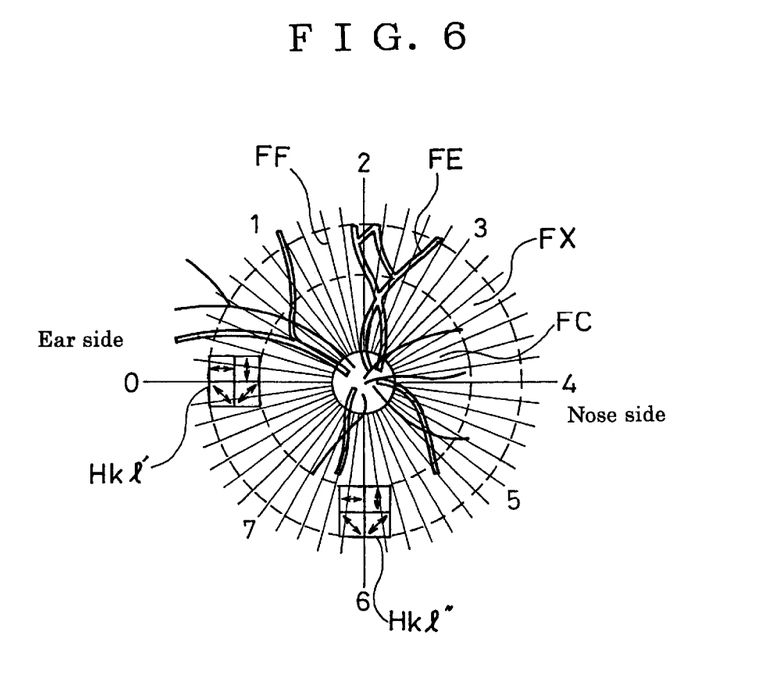
FIG. 6 is a schematic illustration of the ocular fundus of a subject to be examined.

On the ocular fundus 41, as schematically shown in FIG. 6, optic nerve fibers FF extend radially from the mammilla FC. The birefringent characteristics of the optic nerve fibers FF differ by nature between the direction of running thereof and the direction perpendicular thereto.

When the eye is normal, the thickness of the nerve fiber layers increases toward the mammilla FC and decreases as the distance from the mammilla FC increases.

A portion on the ocular fundus irradiated with the circularly polarized green wavelength light causes a change in phase difference owing to the birefringent effect of the optic nerve fibers FF at that portion. The change in this phase difference increases as the thickness of the nerve fiber layers FF increases.

The change in phase difference in circularly polarized light corresponds to the phenomenon that circularly polarized light changes into elliptically polarized light, and the flatness of the ellipse corresponds to the change in phase difference from circularly polarized light.

Thus, it can be said that the flatness of elliptically polarized light is greater when the thickness of the nerve fiber layers FF is greater.

On the contrary, that portion of an ocular fundus which is deficient in optic nerve fibers FF from some or other cause shows no birefringent effect and the state of the circularly polarized light irradiated on the portion of ocular fundus is conserved as it is.

In this way, the illuminating light differing in polarized state depending on the presence or the thickness of the nerve fiber layers FF as reflected by the ocular fundus 41 is led, through the objective lens 30, perforated mirror 29 opening 43, imaging diaphragm Y, focusing lens 32 and relay lenses 33, to the polarizing filter 42. If the unit platelet Hkl of this polarizing filter 42 corresponds to a fundus portion Hkl' shown in FIG. 6, then the reflected light from this fundus portion Hkl' passes through the unit platelet Hkl and forms an image on the four pixels Gij corresponding to that unit platelet.

Figure 5:
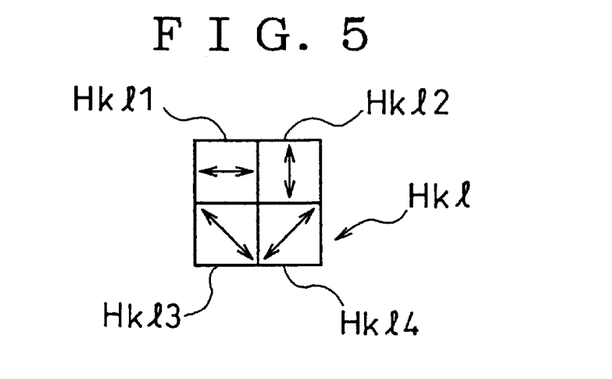
FIG. 5 is an enlargement view of the unit platelet shown in FIG. 4.

On that occasion, the polarizing microplates Hkl1 to Hkl4 of the unit platelet shown in FIG. 5 are disposed so that Hkl1 and Hkl2 respectively correspond to the horizontal direction and vertical direction of the optical system.

On the presumption that, at the ocular fundus portion Hkl', the fluctuation in ocular nerve fiber layers thickness is slight within the portion, the received light output from the four polarizing microplates Hkl1 to Hkl4 and from the corresponding four pixels Gij is regarded as the received light output from one unit platelet Hkl and from the corresponding pixels.

Figure 7A:
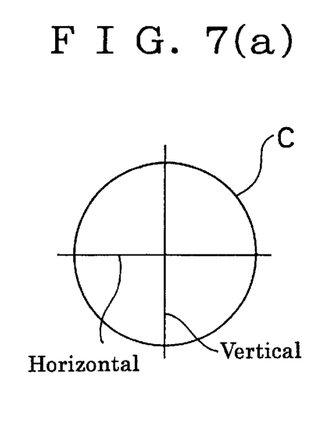

Here, suppose that the ocular fundus is irradiated with circularly polarized light C shown in FIG. 7(a). (In FIG. 7, the horizontal axis and vertical axis respectively correspond to the directions of the polarizing platelets Hkl1 and Hkl2.)

If, then, there are no optic nerve fibers FF at the fundus portion Hkl', the reflected illuminating light from that fundus portion Hkl' conserves the state of circularly polarized light C.

Therefore, the reflected illuminating light passing through each polarizing microplate Hkl1 to Hkl4 of the unit platelet has the same intensity and is received by the corresponding pixel Gij, and the received light outputs from the four pixels are the same.

Figures 7B, 7C:
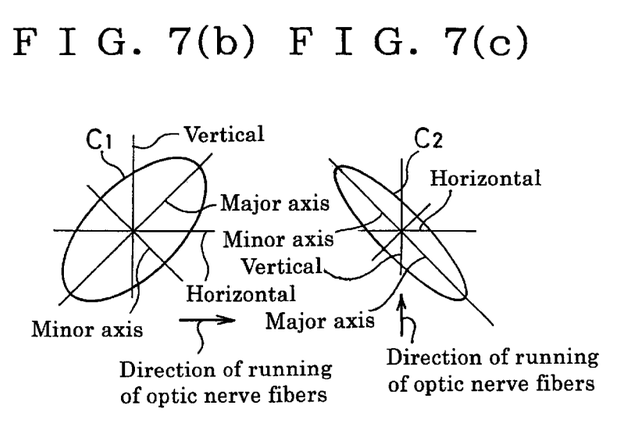

When optic nerve fibers FF are present at that fundus portion Hkl', then the reflected illuminating light from the fundus portion Hkl' is elliptically polarized light C1 as resulting under the influence of the birefringent properties of the optic nerve fibers FF, as shown in FIG. 7(b). The flatness of the elliptically polarized light C1 is proportional to the thickness of the nerve fiber layers FF.

If the unit platelet Hkl of the polarizing filter 42 corresponds to the fundus portion Hkl' shown in FIG. 6, then the reflected light from that fundus portion Hkl' passes through that unit platelet Hkl and makes an image on the corresponding four pixels Gij. If never fiber layers FF are present also at a fundus portion Hkl", the reflected illuminating light from that fundus portion Hkl" becomes elliptically polarized light C2 under the influence of the birefringent properties of the optic nerve fibers FF, as shown in FIG. 7 (c).

When the elliptically polarized reflected illuminating light C1 or C2 entered the polarizing microplate Hkl1 of the unit platelet Hkl, that microplate inhibits other reflected illuminating light components except the polarized light component in the horizontal direction from passing therethrough. Similarly, when the elliptically polarized reflected illuminating light C1 or C2 entered the polarizing microplate Hkl2, that microplate inhibits other reflected illuminating light components than the polarized light component in the vertical direction from passing therethrough. When the elliptically polarized reflected illuminating light C1 of C2 enters the polarizing microplate Hkl3 or Hkl4, that microplate inhibits other reflected illuminating light components except the polarized light component in the direction of an angle of 45° from the horizontal or vertical direction from passing therethrough.

Therefore, when the reflected illuminating light from the fundus portion Hkl' alone is taken into consideration, the received light output from the pixel corresponding to the polarizing microplate Hkl1 becomes maximum, the received light output from the pixel corresponding to the polarizing microplate Hkl2, becomes minimum, and the received light output from the pixel corresponding to the polarizing microplate Hkl3 or Hkl4 is roughly intermediate between the maximum and minimum output.

The explanation made herein is for the case in which the number of microplates is four. However, the shape of the ellipse can be determined from the received light outputs for at least three polarized light components, and the ratio between the minor axis and major axis of the ellipse can be determined therefrom. Therefore, the minimum number of polarizing microplates required is three.

The ratio between the minor and major axis of the ellipse corresponds to the flatness of the ellipse and there is a positive correlation between the flatness of the ellipse and the thickness of the nerve fiber layers, so that by determining the flatness represented by the ratio between the minor and major axis of the ellipse for each fundus portion corresponding to each unit platelet Hkl, it is possible to determine therefrom the change in phase difference as caused at that fundus portion and thereby determine the thickness of the nerve fiber layers at that portion. The computation for determining the layer thickness is conducted using the personal computer.

By reconstructing the fundus image based on the optic nerve fiber FF layer thickness data obtained from the above computation for the respective unit platelets Hkl and displaying the same, it becomes possible to easily grasp the state of deficiency in optic nerve fiber FF layer.

Figure 8:
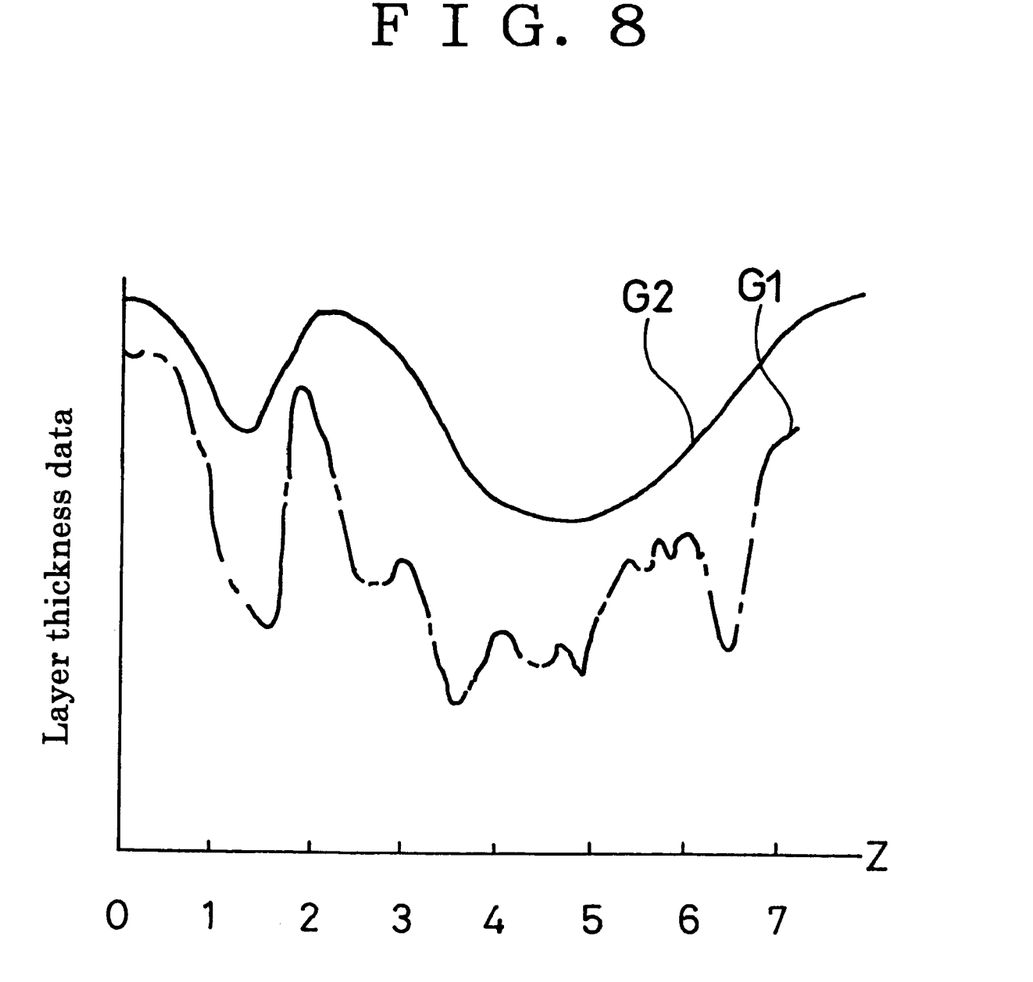
FIG. 8 is a graphic representation of the layer thickness data obtained in an example.

FIG. 8 is a graphic representation of the nerve fiber layers thickness data G1 obtained in an example for the respective fundus portions FX (cf. FIG. 6) resulting from radial division of the ocular fundus therearound with the mammilla FC as the center. The numerals 0 to 7 given along the abscissa of the graph each corresponds to the direction of the fundus portion FX as shown in FIG. 6. The ordinate denotes the layer thickness value.

The data given the symbol G2 are layer thickness data for a normal subject and, by comparing the layer thickness data G1 with the layer thickness data G2, it becomes easier to grasp the state of deficiency in optic nerve fibers FF.

It is desirable that such layer thickness data G2 for normal subjects be stored in a data base as a collection of standard layer thickness data from which adequate standard data can be selected according to the age, race and other factors.

It is also recommendable to use a color CCD camera, for instance, to thereby use only received light output data for green wavelength components in computation.

Figure 9:
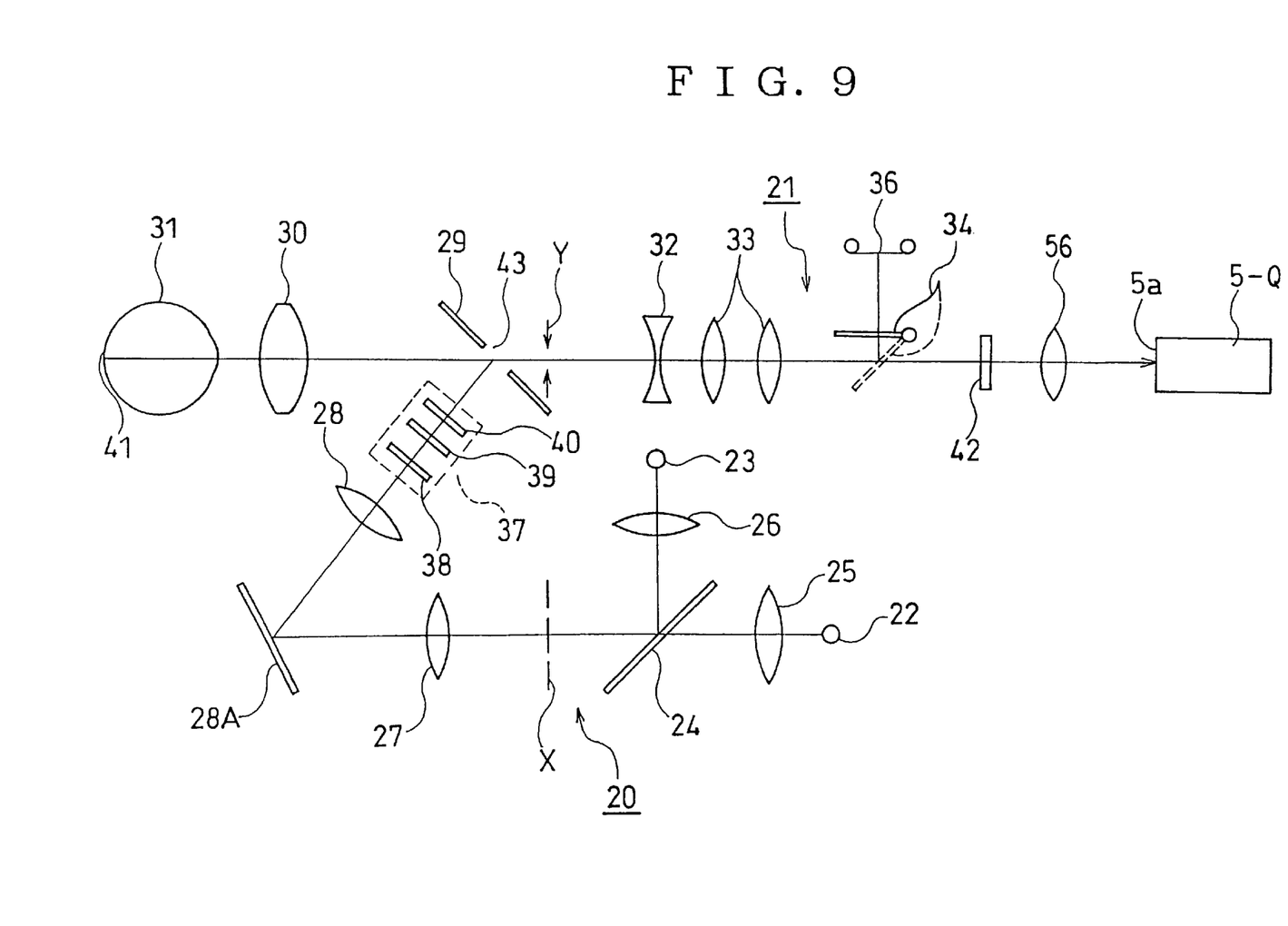
FIG. 9 is an illustration of a modification of the optical system according to embodiment 1 of the invention.

FIG. 9 is a diagram illustrating a modification of embodiment 1 of the invention, which has a constitution such that the polarizing filter 42 is disposed at a conjugated position relative to the ocular fundus 41 and a relay lens 56 is disposed between the polarizing filter 42 and the CCD camera 5-Q so as to make the polarizing filter 42 and imaging surface 5a conjugated, to thereby relayedly forming the fundus image and the image from the polarizing filter 42 on the imaging surface 5a by means of the relay lens 5. The polarizing filter 42 is detachably disposed in the optical path of the imaging optical system 21. During observation, this polarizing filter 42 is kept removed from the optical path of the imaging optical system 21 and, on the occasion of taking a photograph, it is inserted into the optical path of that imaging optical system 21.

By disposing the polarizing filter 42 detachably in the optical path of the imaging optical system 21 in that manner, it becomes possible to observe the fundus image FB even when the polarizing unit 37 is disposed undetachably in the optical path of the illuminating optical system 20.

In this embodiment 1 of the invention as above illustrated, the green filter 38 is disposed in the polarizing unit 37. This is for the reason that the reflectivity of optic nerve fibers FF is greater at the green wavelengths. While it is desirable that this green filter 38 be provided, the present invention can be performed without providing such a filter.

[Embodiment 2 of the invention]

Figure 10:
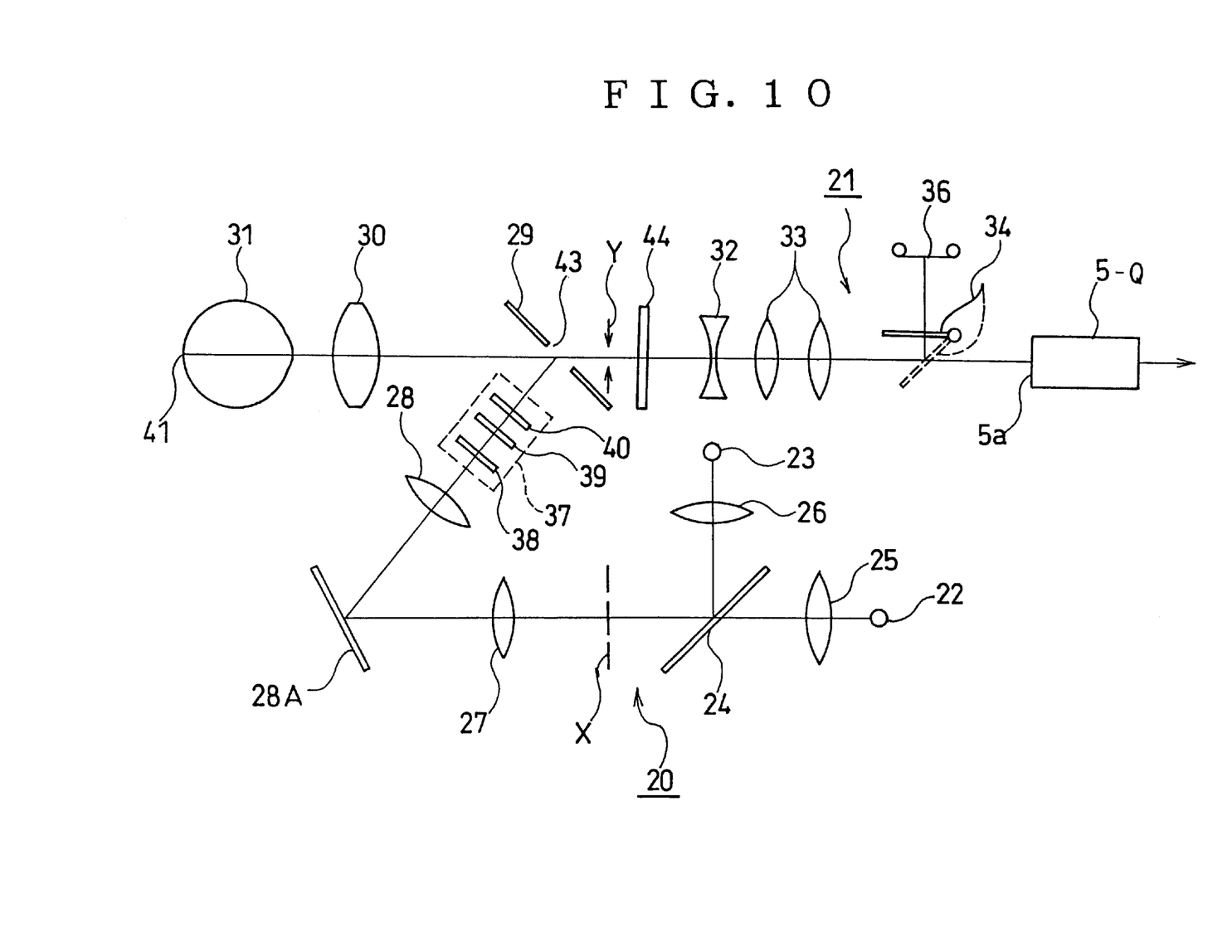
FIG. 10 is an illustration of the optical system according to embodiment 2 of the invention.

In the embodiment shown in FIG. 10, a polarizing filter 44 having linearly polarizing characteristics is provided between the imaging diaphragm Y and focusing lens 32 in place of the polarizing filter 42 comprising polarizing microplates differing in direction of linearly polarized light and disposed in the optical path of the imaging optical system 21 and, by rotating the polarizing filter 44 by 45°, the ocular fundus 41 is photographed four times for conducting nerve fiber FF layers thickness analysis based on the four fundus images.

It is also possible to constitute this polarizing filter 42 as one automatically rotatable in response to the operation by the photographer.

It is further possible to employ a constitution such that a mechanically rotatable polarizing filter 42 and a control device capable of setting an arbitrary angle of rotation of the polarizing filter and the corresponding number of photos to be taken are provided for synchronizing the rotation of the polarizing filter with the timing of CCD photographing. By employing such constitution, it is possible to record a required number of images at respective angles of the polarizing plate in an instant by one exposure operation.

When the ocular fundus portion corresponds to a certain pixel, the circularly polarized illuminating light becomes elliptically polarized light under the influence of the birefringent properties of the optic nerve fibers FF at that portion. Out of components of this elliptically polarized light, only a component in the direction identical with the direction of the linearly polarized light of the polarizing filter 44 (component in a predetermined direction) is transmitted by the polarizing filter 44 and other components of the reflected illuminating light are prevented from passing. When this polarizing filter 44 is rotated by 90° from the predetermined direction, this polarizing filter 44 transmits reflected illuminating light comprising a polarized light component orthogonal to the polarized light component in the predetermined direction (reflected illuminating light comprising a polarized light component in the minor axis direction) while other polarized light components are inhibited from passing by the polarizing filter 44. Further, when this polarizing filter 44 is rotated to a 45° position intermediate between the 0° direction and 90° C. direction, the polarizing filter 44 transmits reflected illuminating light comprising a polarized light component in the 45° direction while other reflected illuminating light comprising a polarized light components are inhibited from passing therethrough.

When nerve fiber layers FF run in the horizontal direction, a polarized light tends to flatten elliptically in the direction inclined by 45° from the horizontal direction, hence the received light output of the corresponding pixel tends to become maximum in the 45° direction and minimum in the 135° direction and tends to become intermediate between the maximum and minimum in the vertical (90°) direction.

Therefore, as mentioned above, when at least three received light output data are available for a pixel, the shape of the ellipse can be determined, hence the degree of flatness are represented by the ratio between the minor and major axis of the ellipse can be determined, so that the nerve fiber layers thickness can be determined in the same manner as in embodiment 1 of the invention.

Figure 11:
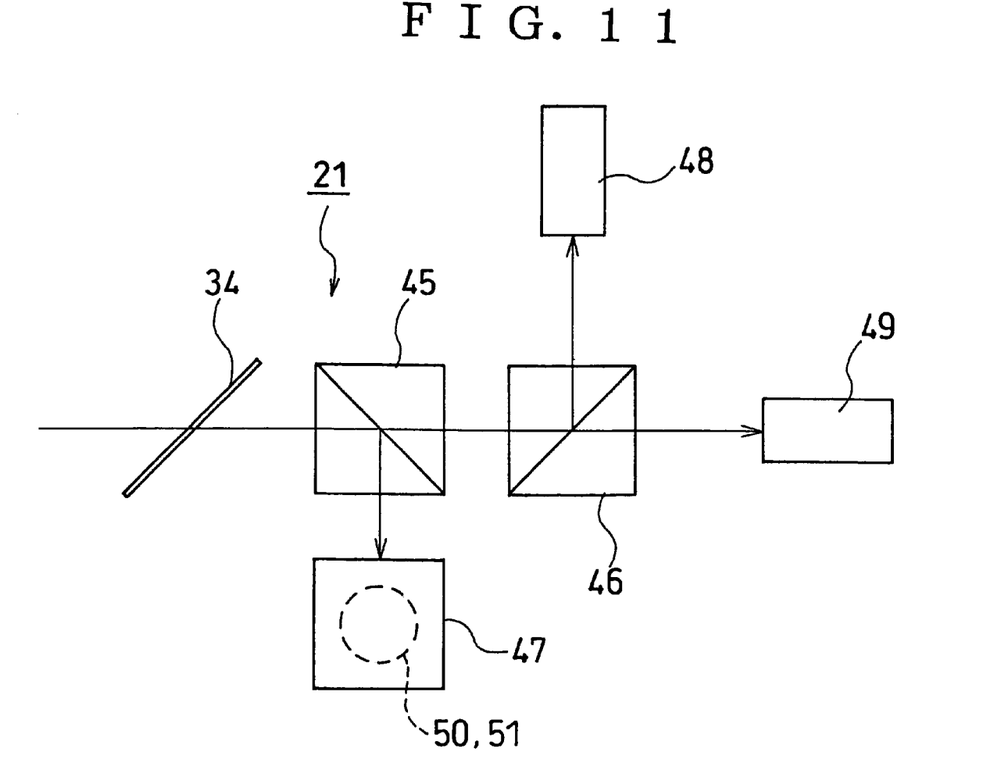
FIG. 11 is a partial illustration of a modification of the optical system according to embodiment 2 of the invention.

FIG. 11 illustrates a modification of embodiment 2 of the invention, according to the constitution of which a polarizing filter 44 is provided in the imaging optical system 21, this polarizing filter 44 is not rotated but polarized light beam splitters 45 to 47 differing in linearly polarizing direction by 45° are provided in the optical path of the imaging optical system 21 and, at the same time, four CCD cameras 48 to 51 are provided at positions conjugated with the ocular fundus 41 for simultaneous photographing of the ocular fundus 41. Since the method of computing the thickness of the nerve fiber layers FF is the same as mentioned hereinbefore, detailed description thereof is omitted.

According to the constitution shown in FIG. 11, the ocular fundus can be photographed at one time and, therefore, the burden on the patient can be alleviated.

EFFECTS OF THE INVENTION

By improving the optical system of a fundus camera in common use so as to provide the glaucoma diagnosis apparatus of the present invention, it is possible to measure the thickness of the nerve fiber layers and diagnose glaucoma.

What is claimed is:

1. A glaucoma diagnosis apparatus comprising an illuminating optical system for illuminating an ocular fundus of a subject to be examined with circularly polarized illuminating light and an imaging optical system including a CCD camera for photographing an image of the ocular fundus based on a reflected illuminating light from said fundus, wherein said CCD camera has a polarizing filter provided integrally with the imaging surface of said CCD camera and said filter is composed of repetitions of a unit platelet being a couple of polarizing microplates transmitting linearly polarized light components that are crossing each other out of said reflected illuminating light and other adjacent polarizing microplate which transmits linearly polarized light components having a direction and which are crossing to said linearly polarized light components that are crossing each other.

2. A glaucoma diagnosis apparatus as claimed in claim 1 wherein the direction of said linearly polarized light components which are crossing to said linearly polarized light components that are crossing each other is in the direction of 45° relative to said linearly polarized light components that are crossing each other, and each polarizing microplate corresponds to each pixel of said CCD camera.

3. A glaucoma diagnosis apparatus comprising an illuminating optical system for illuminating an ocular fundus of a subject to be examined with circularly polarized illuminating light and an imaging optical system including a CCD camera for photographing an image of the ocular fundus based on a reflected illuminating light from said fundus, wherein the imaging optical system is provided at a position conjugated with the imaging surface of said CCD camera with a polarizing filter composed of repetitions of a unit platelet being a couple of polarizing microplates one of which resolves said reflected illuminating light into linearly polarized light components that are crossing orthogonally to each other and another polarizing microplate which resolves said reflected illuminating light into linearly polarized light components having a direction and which are crossing to said linearly polarized light components that are crossing orthogonally to each other.

4. A glaucoma diagnosis apparatus as claimed in claim 3 wherein the direction of said linearly polarized light components which are crossing to said linearly polarized light components that are crossing orthogonally to each other is in the direction of 45° relative to said linearly polarized light components that are crossing orthogonally to each other, and each polarizing microplate corresponds to each pixel of said CCD camera.

5. A glaucoma diagnosis apparatus as claimed in claim 2 or 4 wherein a shape of elliptically polarized light is computed based on magnitude of the output of each pixel corresponding to each polarizing microplate constituting said unit platelet and thickness of the nerve fiber layers of said ocular fundus is determined based on said shape of the elliptically polarized light.

6. A glaucoma diagnosis apparatus as claimed in claim 3 or 4 wherein said polarizing filter is arranged insertably into and retractably from an optical path of said imaging optical system.

7. A glaucoma diagnosis apparatus as claimed in any one of claims 1–4 wherein a green filter for transmitting green light is provided in said illuminating optical system.

* * * * *